(12) United States Patent
Smith et al.

(10) Patent No.: US 8,420,740 B2
(45) Date of Patent: Apr. 16, 2013

(54) METHOD TO REPAIR A DAMAGED INTERVERTEBRAL DISC THROUGH THE USE OF A BIOADHESIVE, THERMOGELLING HYDROGEL

(75) Inventors: Nigel Gordon Smith, Norwich (GB); Meredith Hans, Abington, PA (US); Anthony M. Lowman, Wallingford, PA (US); Andrea Jennifer Vernengo, Sicklerville, NJ (US); Garland Fussell, Thorndale, PA (US)

(73) Assignees: Synthes USA, LLC, West Chester, PA (US); Drexel University, Philadelphia, PA (US)

( * ) Notice: Subject to any disclaimer, the term of this patent is extended or adjusted under 35 U.S.C. 154(b) by 294 days.

(21) Appl. No.: 11/842,705

(22) Filed: Aug. 21, 2007

(65) Prior Publication Data
US 2008/0076852 A1  Mar. 27, 2008

Related U.S. Application Data

(60) Provisional application No. 60/840,383, filed on Aug. 25, 2006.

(51) Int. Cl.
*C08K 9/06* (2006.01)
*C08L 35/00* (2006.01)
*C08F 283/00* (2006.01)

(52) U.S. Cl.
USPC .......... 525/217; 525/207; 525/540; 523/113; 424/486

(58) Field of Classification Search .......... 430/495; 424/486, 488; 514/2, 55, 57; 523/113; 525/55, 525/217, 221, 231, 540
See application file for complete search history.

(56) References Cited

U.S. PATENT DOCUMENTS

| | | |
|---|---|---|
| 6,719,797 B1 | 4/2004 | Ferree |
| 6,770,740 B1 * | 8/2004 | Rice et al. .......... 530/300 |
| 6,818,018 B1 * | 11/2004 | Sawhney .......... 623/11.11 |
| 2004/0220296 A1 * | 11/2004 | Lowman et al. .......... 523/113 |
| 2005/0203206 A1 | 9/2005 | Trieu |

FOREIGN PATENT DOCUMENTS

| | | |
|---|---|---|
| WO | WO00/45868 | 8/2000 |
| WO | WO2004/098756 | 11/2004 |
| WO | WO2007/067622 | 6/2007 |

OTHER PUBLICATIONS

Thomas et al. "Development of Injectable Hydrogels for Nucleus Pulposus Replacements." Drexel University, Jun. 2006, pp. 1-212.*
Twaites et al. "Thermoresponsive Polymers as Gene Delivery Vectors: Cell Viability, DNA Transport, and Transfection studies." Journal of Controlled Release. Oct. 7, 2005, pp. 472-483.*
Matsuda et al. "Bioadhesion of gelatin films crosslinked with Glutaraldehyde." Research Center for Biomedical Engineering. Sep. 10, 1998, pp. 20-27.*
Int'l Search Report issued Jan. 13, 2009 in a corresponding appln.
Xu et al., pH-and temperature-responsive hydrogels from crosslinked triblock copolymers prepared via consecutive atom transfer radical polymerizations, Biomaterials, vol. 27, No. 14, May 1, 2006 (relevance listed in search report).

* cited by examiner

*Primary Examiner* — Hannah Pak
(74) *Attorney, Agent, or Firm* — Stradley Ronon Stevens & Young, LLP

(57) ABSTRACT

The present invention is directed to a bioadhesive thermogelling hydrogel composition for repairing and/or augmenting an intervertebral disc. The bioadhesive thermogelling hydrogel composition can be cross linked with the surrounding tissue so as to potentially serve as a nucleus pulposus replacement or augmentation along with serving to repair annular tears or fissure. The bioadhesive thermogelling hydrogel composition may include three main components: a thermal responsive polymer, an amine-containing polymer and a crosslinking component. All three components can be modified and combined in numerous ways to serve the need of the system as long as the amine-containing component is kept separate from the crosslinking component until the components are injected. The incorporation of a two-part crosslinking thermal responsive hydrogel permits smaller amounts of the crosslinking component to be used and enables the crosslinking dialdehyde to be delivered locally into the tissue that will react with the hydrogel. This helps prevent damage to tissues away from the hydrogel.

17 Claims, 16 Drawing Sheets

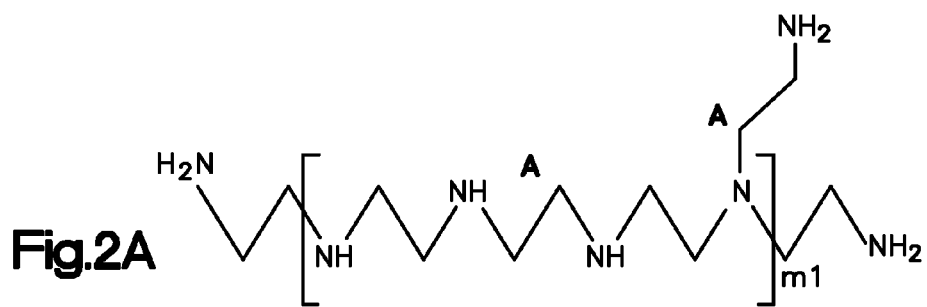
Fig.2A
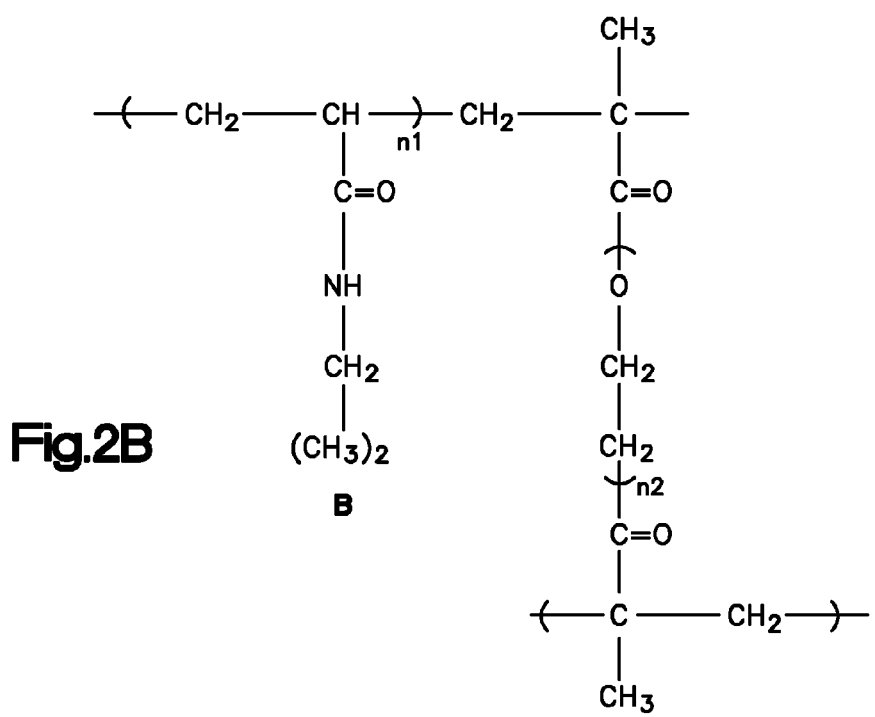
Fig.2B
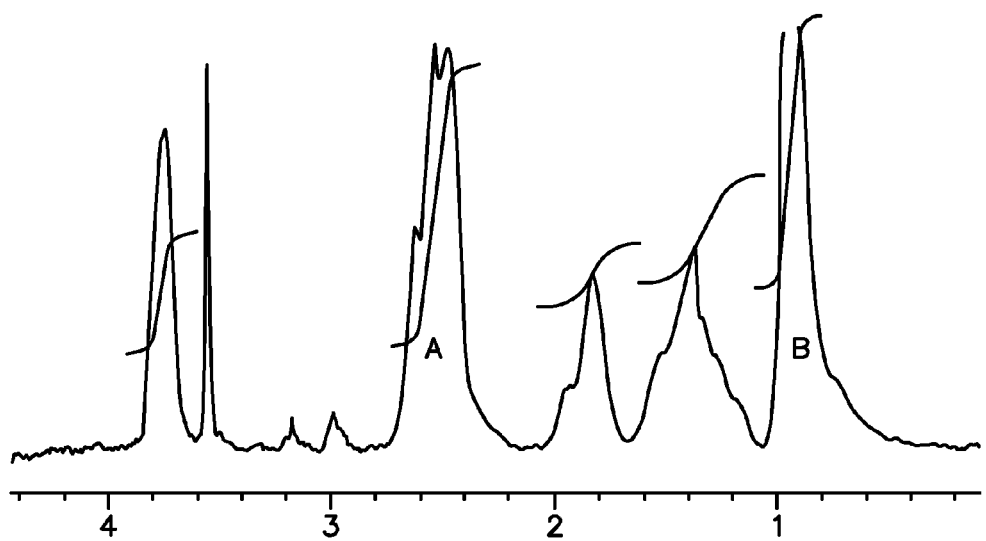
Fig.2C   CHEMICAL SHIFT (ppm)

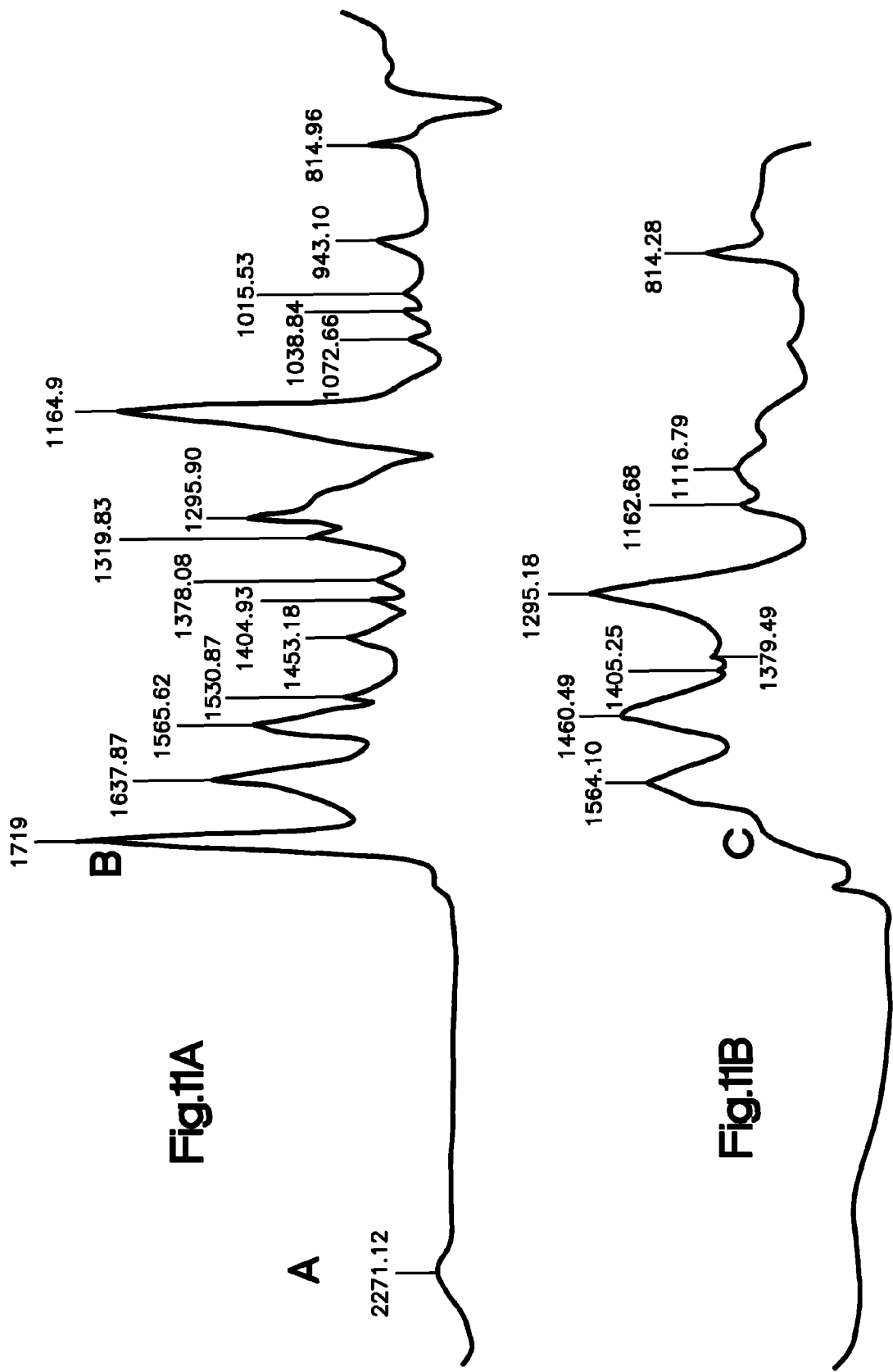

US 8,420,740 B2

METHOD TO REPAIR A DAMAGED INTERVERTEBRAL DISC THROUGH THE USE OF A BIOADHESIVE, THERMOGELLING HYDROGEL

CROSS REFERENCE TO RELATED APPLICATIONS

This application claims priority to U.S. Provisional Patent Application No. 60/840,383, filed on Aug. 25, 2006, the contents of which are incorporated herein by reference.

FIELD OF THE INVENTION

The present invention relates to an apparatus and/or method for repairing or supplementing an intervertebral disc and more particularly to an apparatus and/or method for repairing or supplementing a nucleus pulposus of an intervertebral disc using a bioadhesive thermogelling hydrogel.

BACKGROUND OF THE INVENTION

The human intervertebral disc is comprised of two major structures, an outer or peripheral tendinous structure, and an inner gelatinous nucleus pulposus located in a generally central region. Degeneration of the nucleus, typically associated with natural aging, leads to disc degradation and loss of function.

Chronic back pain caused by injury or age-related degeneration of an intervertebral disc is a condition experience by many patients. Current treatments range from bed rest to highly invasive surgical procedures, including spinal fusion and total disc replacement.

Replacement or supplementation of the nucleus pulposus can relieve pain, restore healthy physiologic function to the disc and/or prevent additional wear or deterioration on the annulus. Currently, few minimally invasive techniques exist for implantation of hydrogels into a selected site of a mammal. Even fewer techniques can provide the physiological/mechanical properties to restore the damaged disc to its full capacity.

Accordingly, it is desirable to provide a way for repairing a damaged intervertebral disc that overcomes drawbacks of conventional systems and methods. Other objects and advantages of the present invention shall become apparent from the accompanying description and examples.

SUMMARY OF THE INVENTION

Generally speaking, a composition may be provided for repairing a damaged intervertebral disc through the use of a bioadhesive, thermoresponsive hydrogel that can be cross linked with the surrounding tissue so as to potentially serve as a nucleus pulposus replacement or augmentation along with serving to repair annular tears or fissure. The bioadhesive thermogelling hydrogel composition may be formulated with a thermoresponsive polymer component, an amine-containing polymer component and a crosslinking component.

In an exemplary embodiment, the composition may include a thermoresponsive polymer component, an amine-containing polymer component, and a crosslinker. Preferably, the composition is provided in such a manner that the amine-containing polymer and the crosslinker do not react to create crosslinkage until after they have been injected into the desired location.

Preferably, the crosslinker reacts with the amine-containing polymer in the intervertebral disc. The amine-containing polymer is preferably separated from the crosslinker until the thermoresponsive polymer, the amine-containing polymer and the crosslinker are inserted into the intervertebral disc. The thermoresponsive polymer component and the amine-containing component may be inserted into the intervertebral disc collectively and the crosslinker may be inserted into the intervertebral disc after the thermoresponsive polymer component and the amine-containing component have been inserted into the intervertebral disc. Alternatively, the thermoresponsive polymer component and the crosslinker may be inserted into the intervertebral disc collectively and the amine-containing component may be inserted into the intervertebral disc after the thermoresponsive polymer component and the crosslinker have been inserted into the intervertebral disc.

The thermoresponsive polymer composition may be grafted with an amino functional group and a crosslinker. The thermoresponsive polymer component may be reacted to include aldehyde groups to promote crosslinkage. The thermoresponsive polymer may be coupled with a poly(ethylene imine) (PEI). The thermoresponsive polymer can be either blended with PEI or grafted with PEI.

The thermoresponsive polymer component and the amine-containing polymer component may be blended in an aqueous solution. The thermoresponsive polymer component and the amine-containing polymer component may exist as copolymers. The thermoresponsive polymer component may be grafted with a whole or parts of the amine-containing polymer.

The amine-containing polymer component may be an amino functional monomer, the amino functional monomer may be attached to the thermoresponsive polymer component.

A kit for repairing or augmenting an intervertebral disc may also be provided, the kit may include a first compartment having an injectable solution incorporating a thermoresponsive polymer and a first component, and a second compartment incorporating a second component, wherein the first component is selected from one of an amine-containing polymer or a di-functional or multi-functional aldehyde and the second component is the other one of an amine-containing polymer or a di-functional/multi-functional aldehyde.

In yet another exemplary embodiment, the kit for repairing or augmenting an intervertebral disc may include three compartments wherein the first compartment contains a thermoresponsive polymer, the second compartment incorporates an amine-containing polymer and the third compartment contains a di-functional or multi-functional aldehyde.

DESCRIPTION OF THE DRAWINGS

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 2 is a $^1H$ NMR spectrum for PNIPAAm-PEG/PEI blend, in accordance with an exemplary embodiment of the composition;

FIG. 11 is a FTIR spectrum for 2-isocyanatoethyl methacrylate and methacrylate functionalized PEI;

DETAILED DESCRIPTION OF THE PREFERRED EMBODIMENTS

Figure 1:
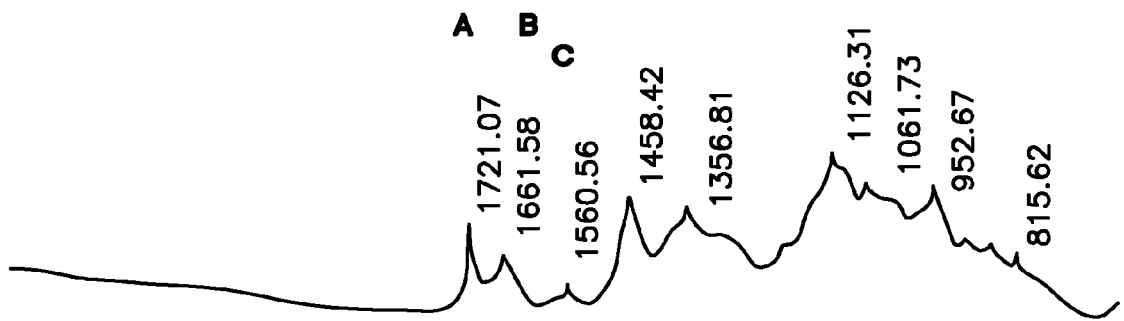
FIG. 1 is a FTIR spectrum for a PEI mixture with glutaraldehyde.

Certain exemplary embodiments of the invention will now be described with reference to the drawings. In general, such embodiments relate to a bioadhesive thermogelling hydrogel composition. The bioadhesive thermogelling hydrogel composition may be formulated with a thermoresponsive polymer component, an amine-containing polymer component and a crosslinking component.

While the bioadhesive thermogelling hydrogel composition will be described as and may generally be used in the spine (for example, in the lumbar, thoracic or cervical regions), those skilled in the art will appreciate that the bioadhesive thermogelling hydrogel composition may be used in other parts of the body such as, for example, joints, long bones or bones in the hand, face, feet, extremities, cranium, etc.

The bioadhesive thermogelling hydrogel composition may include three main components: a thermal responsive polymer, an amine-containing polymer and a crosslinking di-functional or multi-functional aldehyde. All three components can be modified and combined in numerous ways to serve the need of the system as long as the amine-containing component is kept separate from the crosslinking component until the components are injected to the desired in situ location.

At room temperature and prior to injection, the thermoresponsive polymer component, the amine-containing polymer component and the crosslinking component may be individually stored in solution form (e.g. liquid form) allowing for easier injection into the body. The thermoresponsive polymer and the amine-containing polymer component may be simultaneously injected into the intervertebral disc. Alternatively, the thermoresponsive polymer and the amine-containing polymer component may be sequentially injected into the intervertebral disc. Once the thermoresponsive polymer solution warms to body temperature, the thermoresponsive polymer solution undergoes a thermal phase transition to form a solid hydrogel in situ in the body. Specifically, at physiological temperatures, the thermoresponsive polymer solution may undergo a phase transformation to become a hydrophobic polymer, thus forming a hydrogel. The injected amine-containing polymer component may become trapped within the thermoresponsive polymer as gelation occurs. Because amine-containing polymer can be hydrophilic, the hydrogel can swell. The resulting hydrogel may have properties that mimic the biomechanical function of a healthy nucleus. The resulting hydrogel can have the requisite water content and mechanical properties to restore the function of the nucleus.

Next, the hydrogel may then be self-cross linked and reacted to the surrounding tissues, including annular and nucleus tissue through the addition of the crosslinking component, such as a small amount of di-functional dialdehyde monomers or macromers. The amine-containing component and crosslinking component react and create cross-linkages with each other and the surrounding tissue. Alternatively, following injection of the thermally responsive polymer and the amine-containing polymer, the crosslinking component may be injected without waiting for gelation to occur.

Alternatively, the thermoresponsive polymer and the crosslinking component may be simultaneously or sequentially injected into the intervertebral disc, followed by injection of the amine-containing polymer component.

The solutions may be injected into the intervertebral disc space by any means including, but not limited to, via a cannula, needle, syringe, etc.

By separating the amine-containing component from the crosslinking component until injection, the crosslinking component may be injected into thermal responsive polymer component and the amine-containing component thus enabling the creation of cross linking between the amine-containing component and the crosslinking component to preferably occur from the inner region to the periphery as the crosslinking component (e.g. dialdehyde) slowly diffuses through the hydrogel network. Alternatively, the amine-containing component may be injected into thermal responsive polymer component and the crosslinking component. Once the cross linking component reaches the interface between the hydrogel and the tissue, crosslinking of the hydrogel to the tissue preferably occurs and serves to anchor the hydrogel into the intervertebral disc. Such an approach may permit the hydrogel to serve as a nucleus replacement or augmentation device as well as an annular repair or sealant device. The cross linked hydrogel can be applied alone to repair both the annulus and nucleus or in conjunction with another nucleus repair device.

This approach of using multiple part crosslinking thermal responsive hydrogel system permits the use of substantially smaller amounts of the crosslinking component as compared to known in situ curing materials. In addition, using a multiple part crosslinking thermal responsive hydrogel system permits the compositions to be delivered locally into the tissue that will react with the hydrogel. This aids in preventing damage to tissues away from the hydrogel.

The thermoresponsive polymer component may be any thermoresponsive polymer including, but not limited to, copolymers of poly(ethylene oxide) (PEO) and poly(propylene oxide) (PPO), copolymers of PEO and poly(lactic acid) (PLA) as well as other polymers that exhibit a phase transformation between 27-35° C. Preferably, the thermoresponsive copolymer may be PNIPAAm-PEG—a poly(n-isopropyl acrylamide) (PNIPAAm) or its copolymers with poly(ethylene glycol) (PEG). An exemplary embodiment of the thermoresponsive polymer is provided in U.S. patent application Ser. No. 10/837,082 entitled "Thermogelling polymer blends for biomaterial applications," the entire contents of which are expressly incorporated herein by reference. It is believed that at a physiological temperature, hydrogel is formed by physical crosslinks.

An amine-containing, cationic polymer, preferably hydrophilic, component may also be included. Cationic polymers may be any cationic polymer including, but not limited to, poly(diethyl aminoethyl methacrylate), poly(ethyl aminoethyl methacrylate) and other amine-containing polymers. Preferably, the cationic polymer may be poly(ethylene imine) (PEI) as it has a high density of cationic groups along the chain.

A crosslinking component may also be included in the bioadhesive composition. The crosslinking component may be, but is not limited to, multifunctional aldehyde molecules. Preferably, the crosslinking molecule may be di-functional dialdehyde molecules such as, for example, 1-4 butanedial, 1-5 pentanedial, (also called glutaraldehyde), and macromers of di-functionalized PEG-dials. The crosslinking component preferably serves to crosslink the cationic polymer to itself as well as to connect the cationic polymer to the natural tissues that the polymers may contact, promoting overall tissue adhesion. The formation of crosslinks may increase the stiffness of the resulting system and further stabilize the hydrogel network.

The crosslinking chemistry may be illustrated in the following example: in one exemplary embodiment, 8 wt % glutaraldehyde solution (Sigma-Aldrich) was mixed with poly(ethylene imine)(PEI) (Sigma-Aldrich, $M_n$=10,000) in a 1:1 volumetric ratio. An increase in viscosity of the mixture was observed qualitatively within one minute. A color change to light red also occurred. The mixture was lyophilized overnight and analyzed with FTIR (Nicolet Magna IR 560) to verify the amine-aldehyde crosslinking chemistry. FIG. 1 shows the Fourier Transform Infrared (FTIR) difference spectroscopy for the PEI/glutaraldehyde mixture. The crosslinking chemistry between aldehyde groups on the glutaraldehyde and the amine groups on the PEI was verified by the presence of a peak at 1661 cm$^{-1}$ (A), characteristic of the new —C=N— linkage, and 1560 cm$^{-1}$, characteristic of the Amide II band on PEI.

The importance of the crosslinkage and the resulting benefit can be illustrated through the comparison of hydrogel samples injected and not injected with glutaraldehyde. Two sets of hydrogel samples were prepared from an aqueous solution comprising 15% PNIPAAm-PEG (4600 g/mol), 8.5% PEI (Sigma-Aldrich, $M_n$=10,000) was heated to 37° C. to simulate physiological temperature. After gelation occurred, 0.03 mL of aqueous 30 wt % glutaraldehyde (Sigma-Aldrich) was injected into the center of certain cylindrical samples using an 18 gauge needle. Unconfined uniaxial compression tests were then performed. The samples were loaded in an Instron mechanical testing system (Instron Model 4442, Park Ridge, Ill.) and compressed at a strain rate of 100%·min$^{-1}$ while submerged in a 37° C. phosphate buffer saline (PBS) bath. Load and displacement data were recorded with the Instron Series IX software and converted to stress and strain values. The compressive moduli at 10, 15, and 20% strain were approximated as the slope of the chord drawn between 5 and 15% strain, 10 and 20% strain, and 15 and 20% strain, respectively.

For comparison, compression tests were also performed on a second set of samples that were not injected with glutaraldehyde. Both sets were lyophilized for 12 hours following the compression testing. The dry polymer from the second set of hydrogels was dissolved in chloroform (Sigma-Aldrich) and analyzed with nuclear magnetic resonance (NMR) (Varian 300, Palo Alto, Calif.) to quantify the PEI content. Fourier Transform Infrared (FTIR) difference spectroscopy was used to verify the crosslinking chemistry for those hydrogels injected with glutaraldehyde. The infrared (IR) spectrum for PNIPAAm-PEG/PEI blends was subtracted from the spectrum for hydrogels injected with glutaraldehyde to reveal the new bonds formed as a result of the crosslinking.

The successful incorporation of PEI in the PNIPAAm-PEG (4600 g/mol) network was verified with the $^1$H NMR spectrum of the PNIPAAm-PEG/PEI blend in chloroform in FIG. 2. The area of the peak at $\delta$=0.96 ppm for the CH$_3$ protons on isopropyl group of the N-isopropylacrylamide (NIPAAm) was compared to the area of the peak for the CH$_2$ protons on the PEI at $\delta$=2.2 ppm. The calculated ratio of NIPAAm to ethylene imine (EI) monomer units was 6.3:1.

Figure 3:
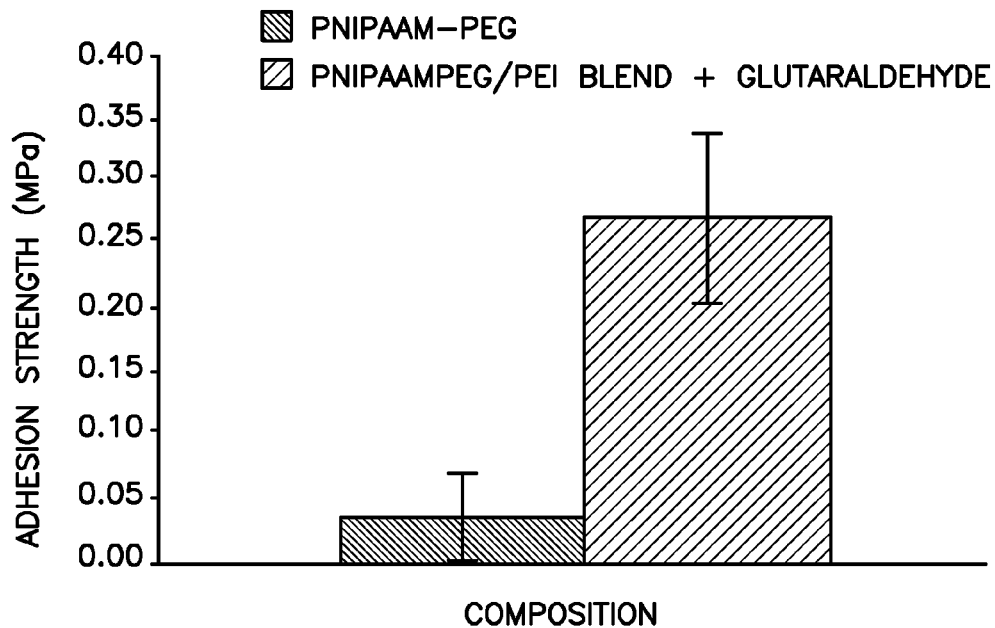
FIG. 3 is a graph showing the comparative adhesion strength between PNIPAAM-PEG and PNIPAAm-PEG/PEI blend+glutaraldehyde.

FIG. 3 shows the adhesion strength of PNIPAAm-PEG/PEI hydrogels with and without glutaraldehyde injection. Hydrogels that were injected with glutaraldehyde show much greater adhesion strength than hydrogels without glutaraldehyde injection.

Figure 4:
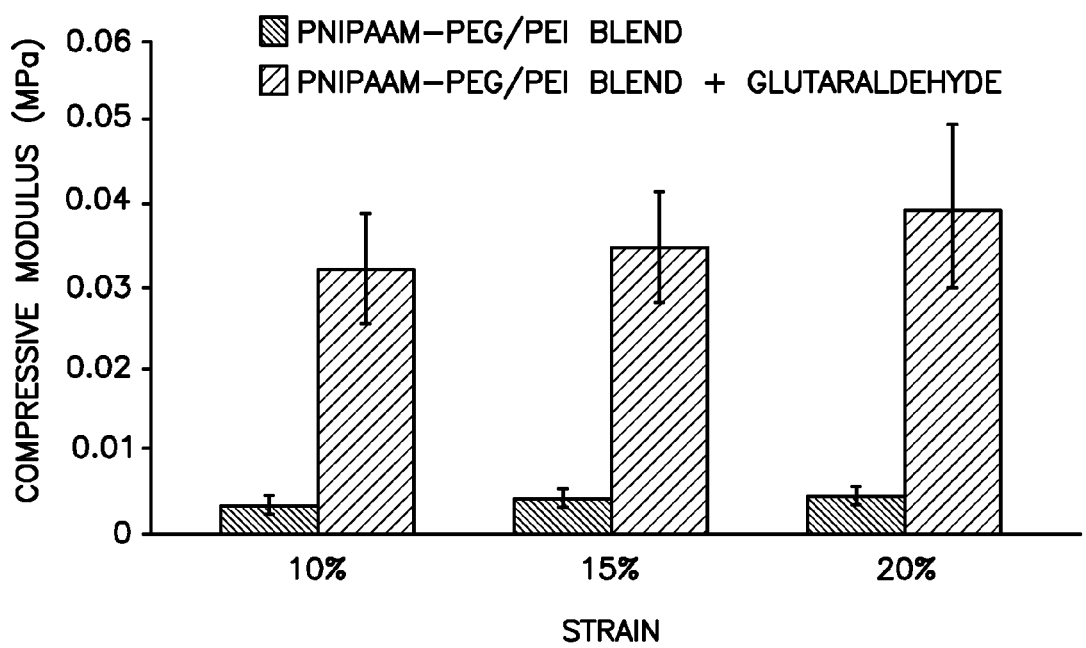
FIG. 4 is a graph showing the comparative modulus between PNIPAAM-PEG and PNIPAAm-PEG/PEI blend+ glutaraldehyde.

FIG. 4 shows the compressive modulus of PNIPAAm-PEG/PEI hydrogels with and without glutaraldehyde injection. Hydrogels that were injected with glutaraldehyde showed significant increase in stiffness as a result of crosslinking between the aldehyde and amine groups.

Figure 5:
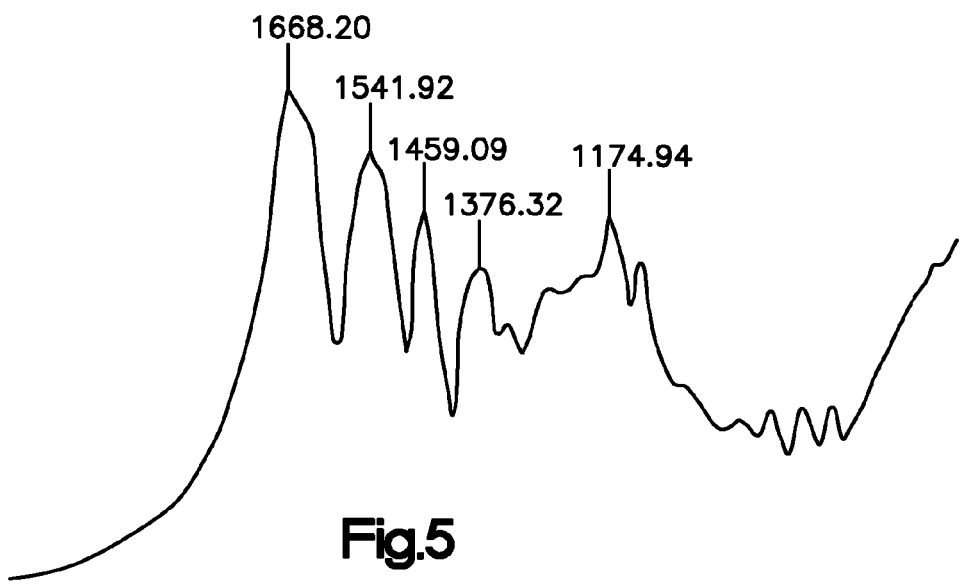
FIG. 5 is a FTIR spectrum for PNIPAAm-PEG/PEI blends injected with glutaraldehyde.

FIG. 5 shows the FTIR spectrum for PNIPAAm-PEG/PEI hydrogels cross-linked by glutaraldehyde. The peak at 1668 cm$^{-1}$ represents the new —C=N— cross-linked formed from the free amine NH$_2$ on PEI and the HC=O aldehyde group on the glutaraldehyde. The peak at 1541 cm$^{-1}$ represents the Amide II band for PEI (HN=C). The peaks for the Amide I and II bands on PNIPAAm (1652 and 1540 cm$^{-1}$, respectively) have been subtracted out due to overlap with peaks of interest for the crosslinking chemistry.

Each of the three components can be modified. Either the amine-containing polymer component or the crosslinking component can be blended or reacted with the thermoresponsive polymer component before injection. However, amine-containing polymer component must be kept separately from crosslinking component until in situ injection.

In one embodiment, PNIPAAm-PEG is blended with PEI. In another embodiment of the invention, copolymers of PNIPAAm-PEG are grafted with PEI, in which the PEI is covalently attached to the PNIPAAm-PEG. This can potentially allow for better chain interpenetration into the tissue allowing for a better connection to the tissue. Yet another embodiment of the invention including combining the thermoresponsive components with the amine-containing component by attaching amino functional monomers in the backbone of the PNIPAAm-PEG copolymer by reacting amino functional monomers such as 2-diethylaminoethyl methacrylate (DAEEM) with the NIPAAm and PEG monomers to covalently link amino functional groups to the copolymer.

Figure 6:
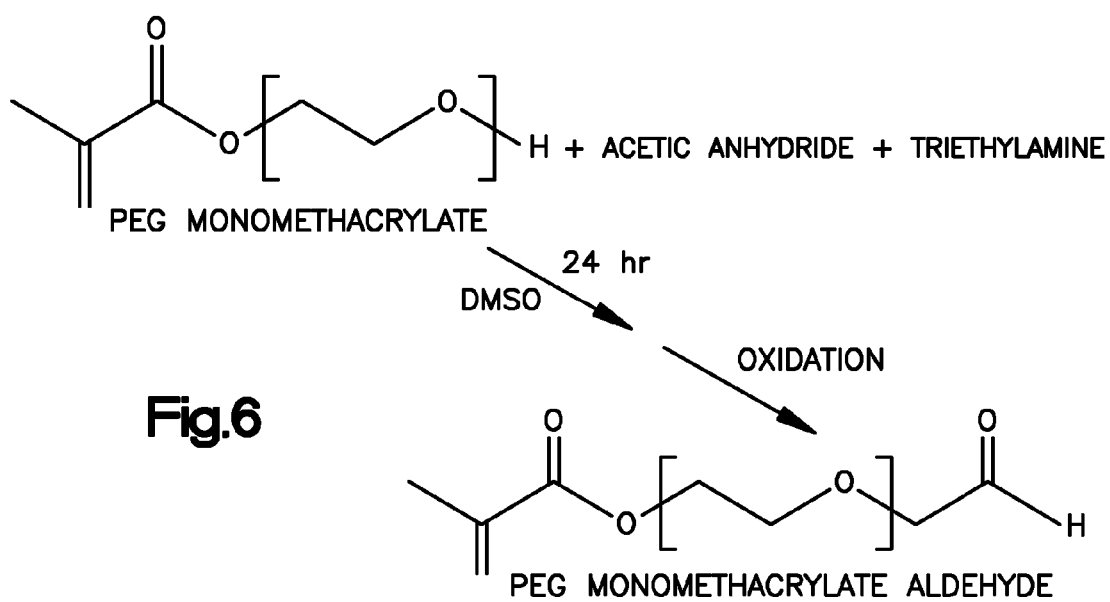
FIG. 6 is a reaction scheme for synthesis of PEG monomethacrylate aldehyde.
Figure 7:
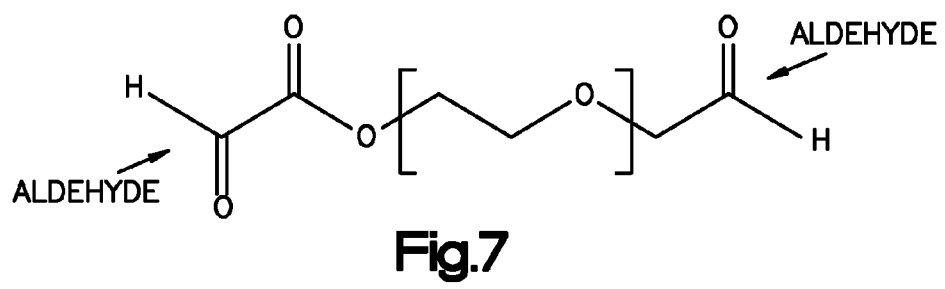
FIG. 7 is a chemical formula of PEG-dialdehyde.

Furthermore, aldehyde groups can be conjugated to one end of a PEG chain that possesses a methacrylate group on the other end, as shown in FIG. 6. The methacrylate group can be reacted in the presence of NIPAAm monomer to form a copolymer. The aldehyde can then be further reacted to crosslink the material or covalently linked with surrounding tissues. Alternatively, aldehyde groups can be conjugated to the ends of PEG chains to synthesize PEG-dialdehyde. FIG. 7 shows the chemical formula of PEG-dialdehyde.

Figure 8:
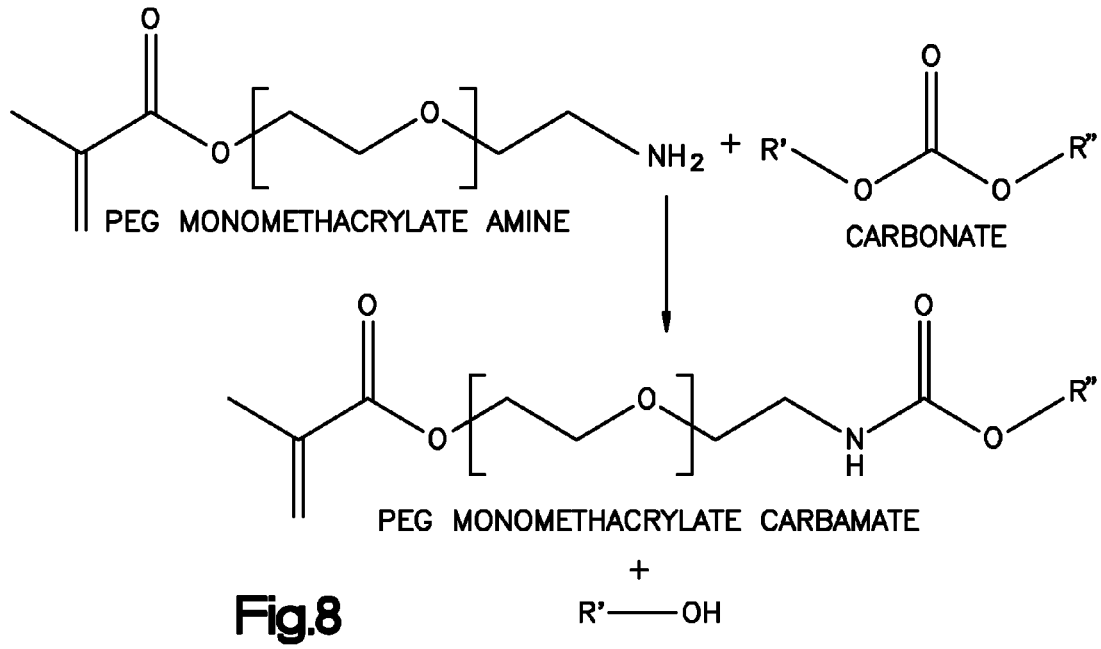
FIG. 8 is a reaction scheme for synthesis of urethane linkage by reacting amine terminated PEG monomethacrylate with a carbonate.
Figure 9:
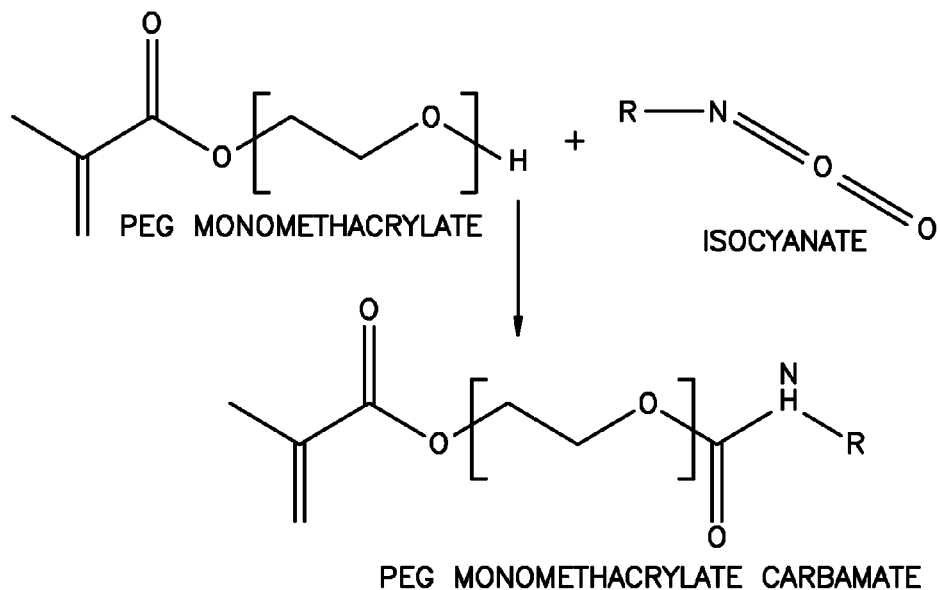
FIG. 9 is a reaction scheme for synthesis of urethane linkage by reacting PEG monomethacrylate with an isocyanate.

In addition to the modifications to the components, there can be a number of methods to promote the in situ curing/tissue adhesion. These methods include reacting amino functionalized materials with a carbonate group to promote crosslinking and tissue adhesion by the creation of stable urethane linkages. The urethane linkages can be used to incorporate tissue adhesive group to PEG chains. This involves reacting a PEG containing a primary amine end group on one or both ends of the chain with a carbonate to form a urethane carbamate linkage, as shown in FIG. 8. In addition, PEG-diol can be reacted with isocyanates to create stable urethane linkages. This example involves reacting a PEG containing an alcohol end group on one or both ends of the chain with an isocyanate to form a urethane carbamate linkage (as shown in FIG. 9).

Preferred embodiments of the invention will be illustrated with reference to the following examples of polymer formulations, which are presented by way of illustration only and should not be construed as limiting.

Example I

Coupling PEI and 2-Isocyanatoethyl Methacrylate

Figure 10:
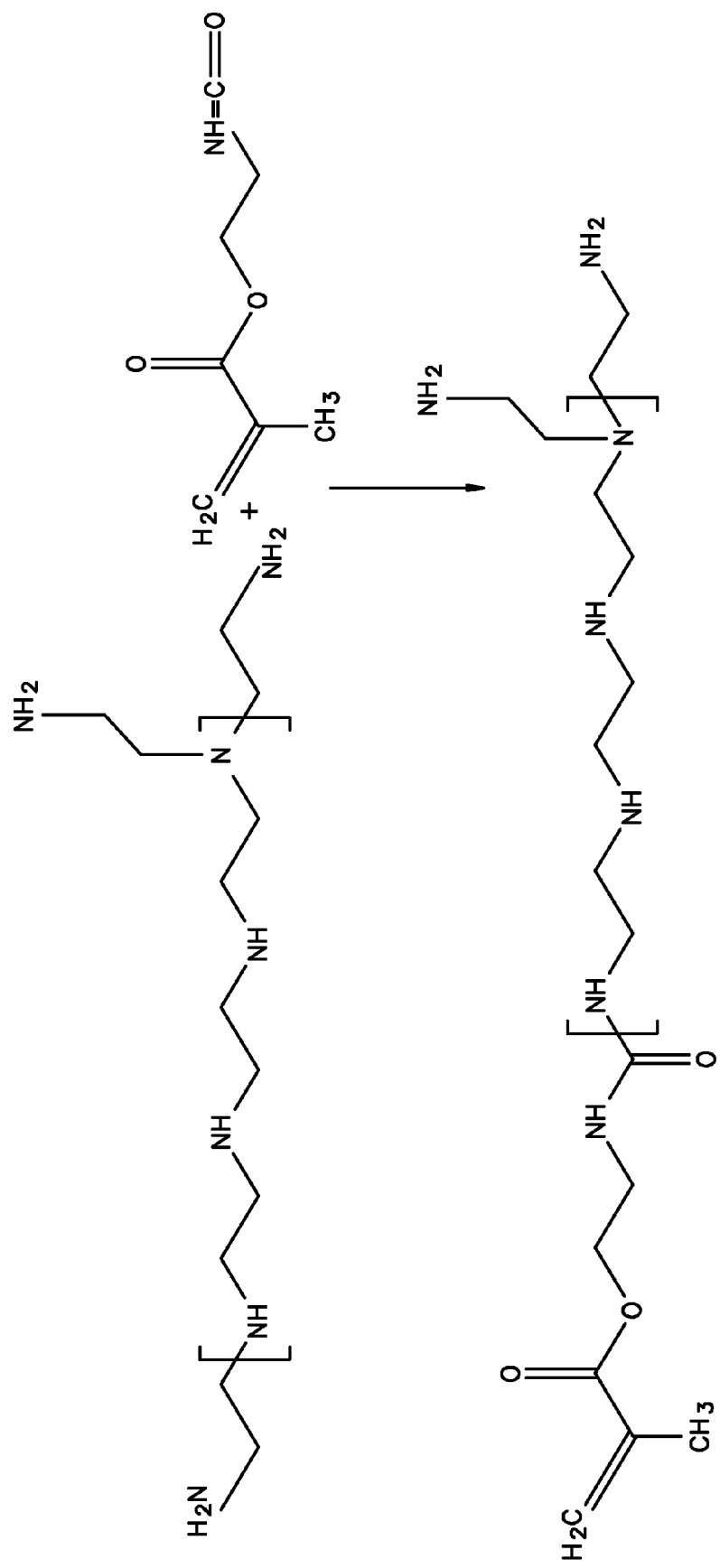
FIG. 10 is a reaction scheme for coupling of 2-isocyanatoethyl methacrylate and PEI.

2-Isocyanatoethyl methacrylate (Sigma-Aldrich) and 10× molar excess PEI (Sigma Aldrich, $M_n$=600 g/mol) were dissolved in dry chloroform and reacted for 12 hours at 60° C. (see FIG. 10). The chloroform was removed from the reaction mixture with a rotary evaporator. This reaction product was then characterized using spectroscopic methods. $^1$H NMR and $^{13}$C NMR spectra were recorded in chloroform (Varian 300, Palo Alto, Calif.). FTIR was conducted on a Nicolet Magna IR 560.

The IR spectrum for 2-isocyanatoethyl methacrylate (see FIG. 11, top) shows absorption for the isocyanate at 2271 cm$^{-1}$ and one for the urethane carbonyl at 1719 cm$^{-1}$. After the reaction, the IR spectrum for the product (see FIG. 11, bottom) shows a peak at 1620 cm$^{-1}$ for the urea bond formed from linking the 2-isocyanateothyl methacrylate and PEI and an absence of the peak for the isocyanate.

Figure 12A:
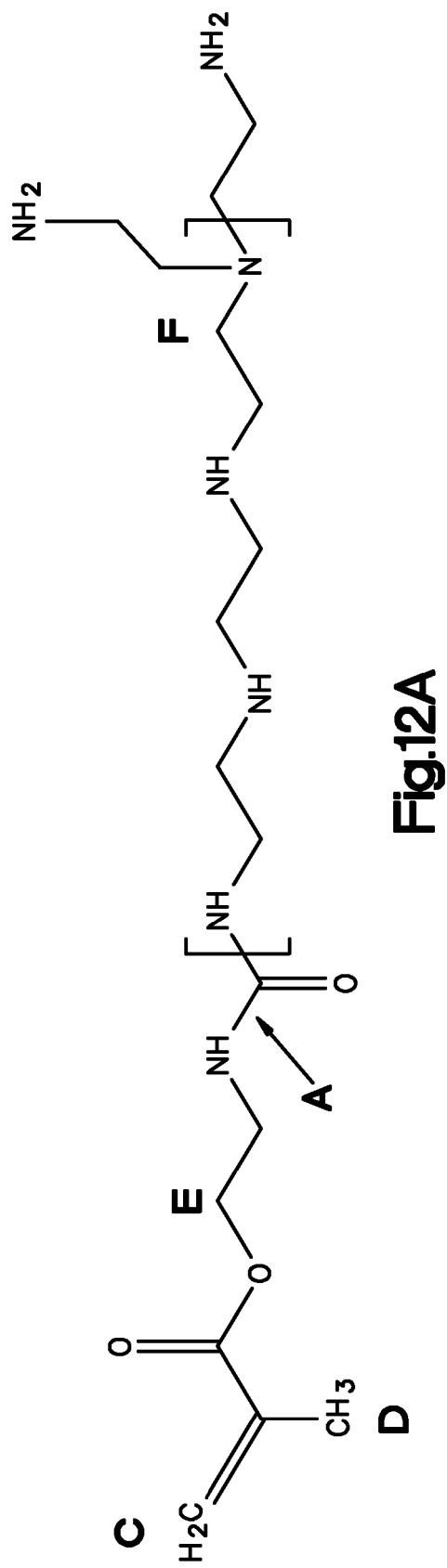
FIG. 12 is a $^{13}$C NMR spectrum for methacrylate functionalized PEI.
Figure 12B:
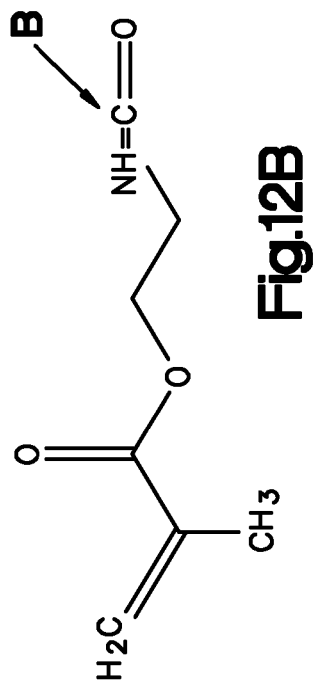
Figure 12C:
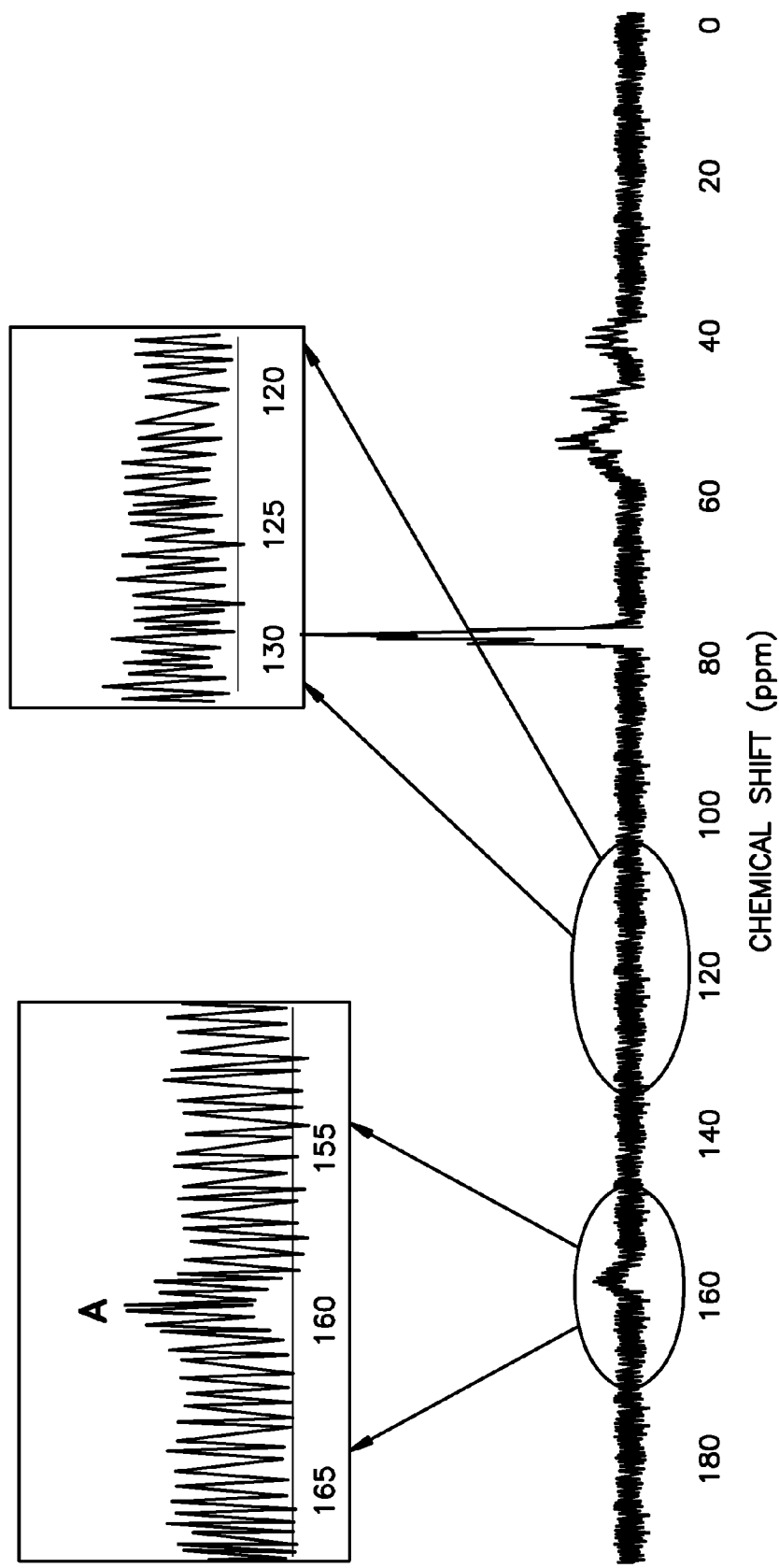

FIG. 12 shows the $^{13}$C NMR spectrum for the same reaction product. The spectrum shows a characteristic signal at 159 ppm for the urea carbonyl (A) and an absence of the signal at 122 ppm for the urethane carbonyl (B) on the unreacted isocyanate group. These results are consistent with the FTIR spectrum in FIG. 11 and indicate successful coupling of the PEI and 2-isocyanatoethyl methacrylate.

Figure 13:
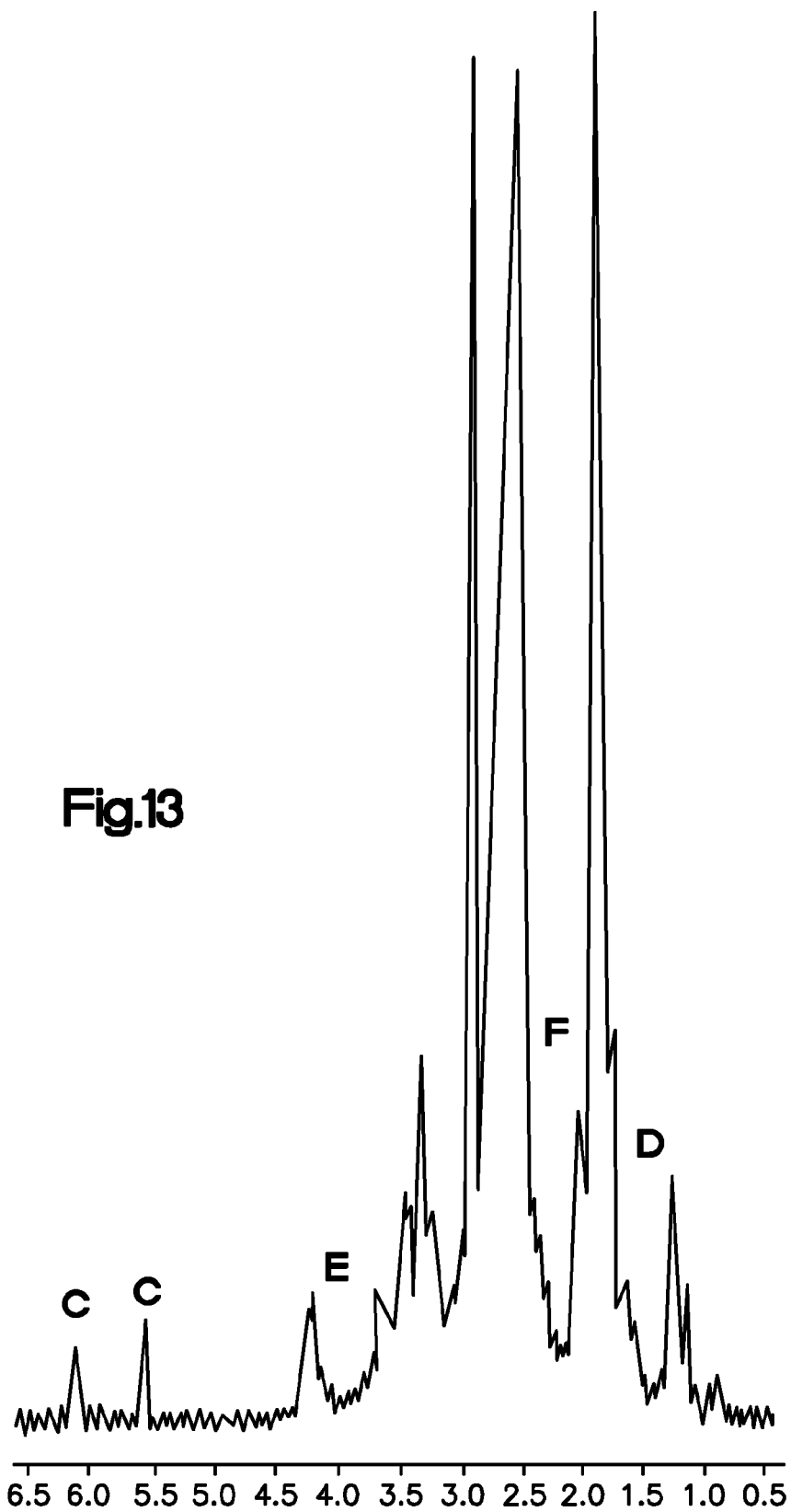
FIG. 13 is a $^1$H NMR spectrum for methacrylate functionalized PEI.

FIG. 13 shows the $^1$H NMR spectrum for the methacrylate functionalized PEI. There are characteristic peaks for the vinyl protons on the methacrylate end group (C) at 5.5 and 6.1 ppm, methyl protons on the methacrylate group (D) at 1.6 ppm, —(O—CH$_2$—CH$_2$) protons on the 2-isocyanatoethyl methacrylate (E) at 4.0 ppm, and the multi-amino groups on the PEI (F) at 2.2 ppm.

Example II

Synthesis of PNIPAAM-PEI Grafted Copolymer

Figure 14:
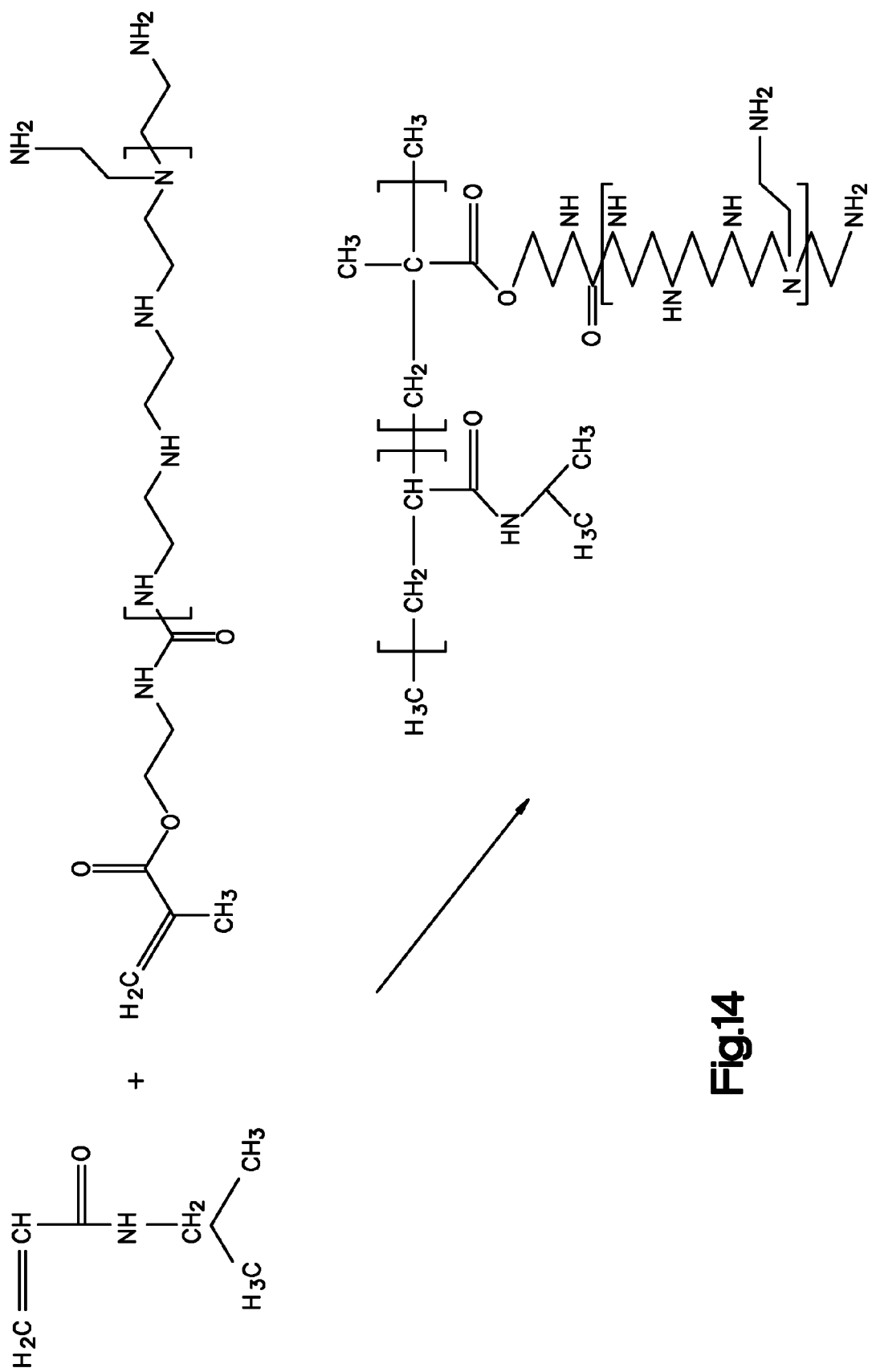
FIG. 14 is a reaction scheme for synthesis of PNIPAAm-PEI branched copolymer.

The methacrylate functionalized PEI and N-isopropylacrylamide (NIPAAm) monomers (Acros Organics) were copolymerized in chloroform at 65° C. for 48 hours (FIG. 14). The reaction was initiated by 2,2'-azobisisobutyronitrile (AIBN). The chloroform was evaporated from the reaction mixtures after polymerization was complete. The unreacted NIPAAm monomer was removed by heating the product to 45° C. in n-hexane. The purified polymer was isolated by vacuum filtration and dried under vacuum overnight. $^1$H NMR and $^{13}$C NMR spectrum were recorded in chloroform (Varian 300, Palo Alto, Calif.).

Figure 15A:
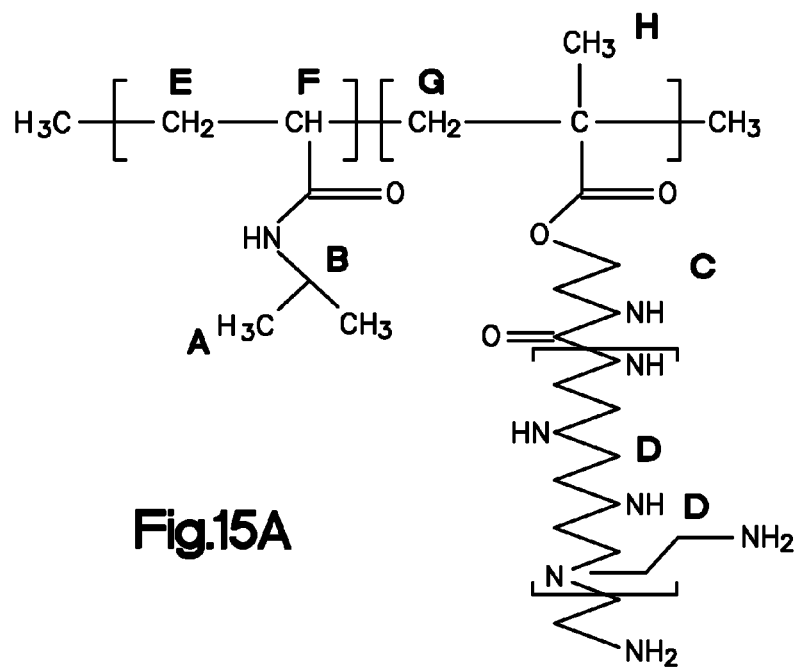
FIG. 15 is a $^1$H NMR spectrum for PNIPAAm-PEI grafted copolymer.
Figure 15B:
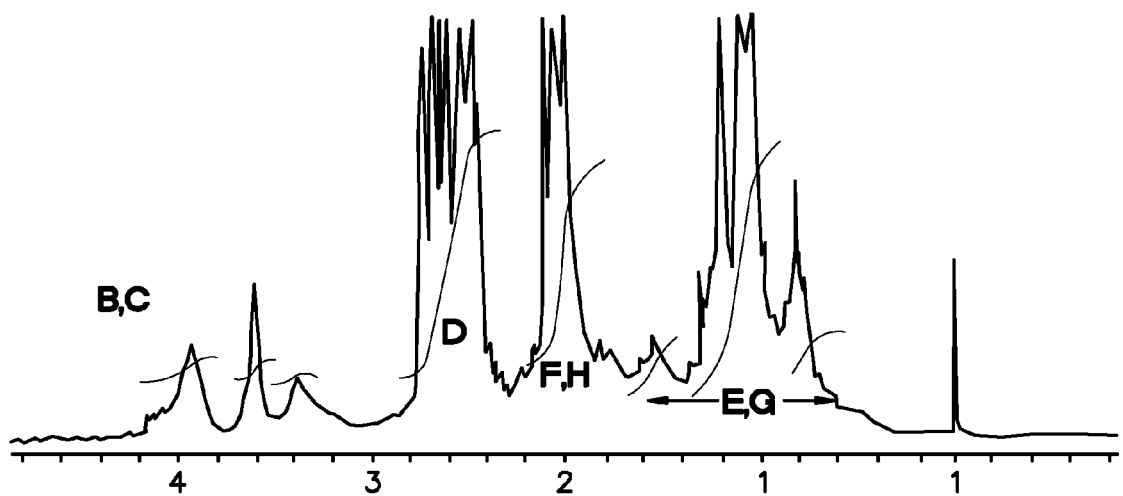

FIG. 15 shows the $^1$H NMR spectrum for a PNIPAAm-PEI graft copolymer. Characteristic peaks are present for both components in the copolymer.

Example III

Copolymerization of 2-DEAE Metharcylate and NIPAAm Monomer

Figure 16:
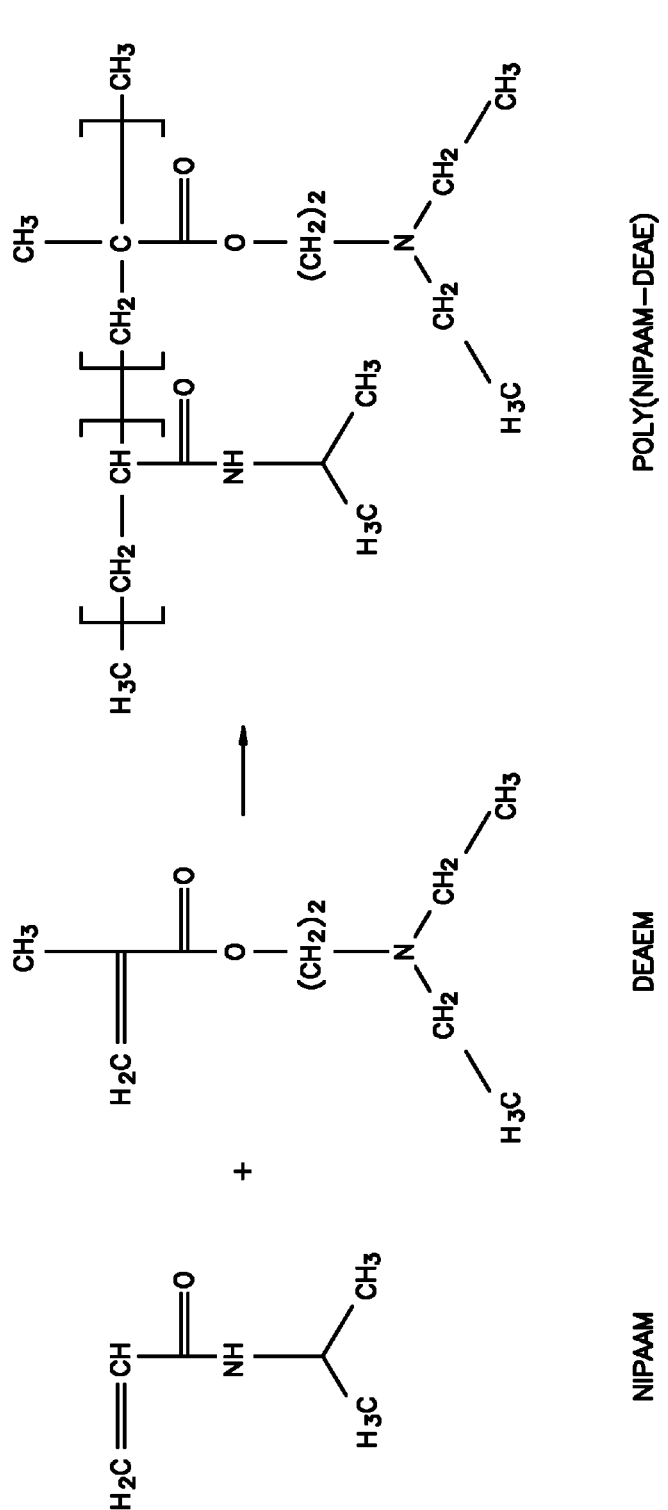
FIG. 16 is a reaction scheme for copolymerization of NIPAAm and 2-diethylaminoethyl methacrylate.

The 2-diethylaminoethyl (2-DEAE) methacrylate (Sigma-Aldrich) and NIPAAm monomer (Acros Organics) were copolymerized in methanol at 65° C. for 48 hours (see FIG. 16). The reaction was initiated by azobisisobutyronitrile (AIBN). The methanol was evaporated from the reaction mixtures after polymerization was complete. The unreacted NIPAAm monomer was removed by heating the product to 45° C. in n-hexane. The purified polymer was isolated by vacuum filtration and dried under vacuum overnight. The purified product was analyzed in chloroform with $^1$H NMR and $^{13}$C NMR (Varian 300, Palo Alto, Calif.).

Figure 17A:
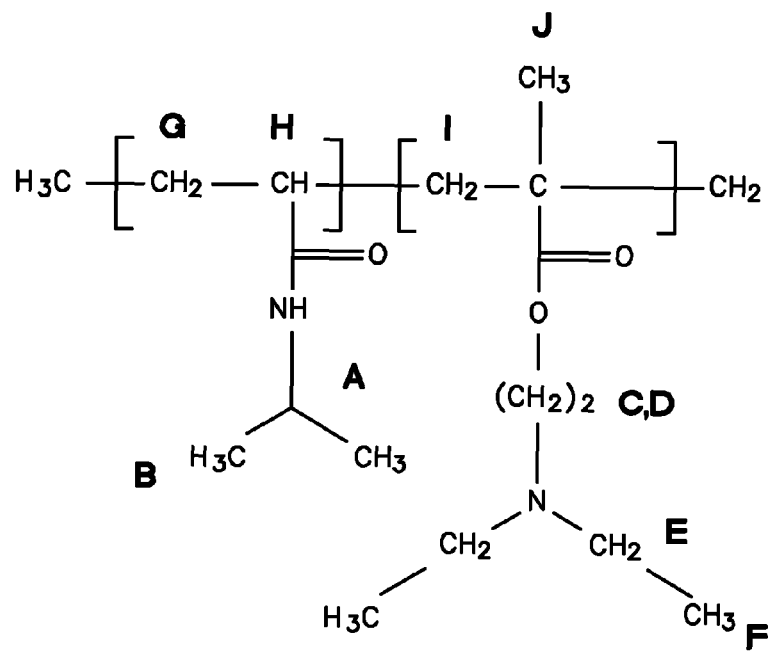
FIG. 17 is a $^1$H NMR spectrum for poly(NIPAAm-DEAE)
Figure 17B:
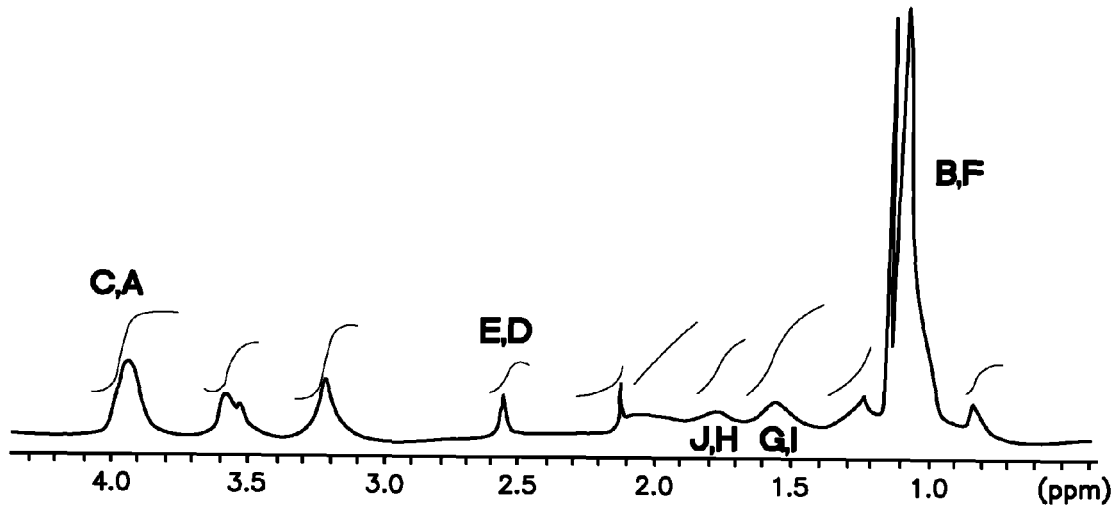

FIG. 17 shows the $^1$H NMR spectrum for the poly (NIPAAm-DEAE) copolymer. There are characteristic peaks present for both components in the copolymer. Due to peak overlap, component ratios can be estimated from peak intensities in the $^{13}$C spectrum (data not shown).

Example IV

PEG Monomethacrylate-Monoaldehyde Synthesis

Figure 18:
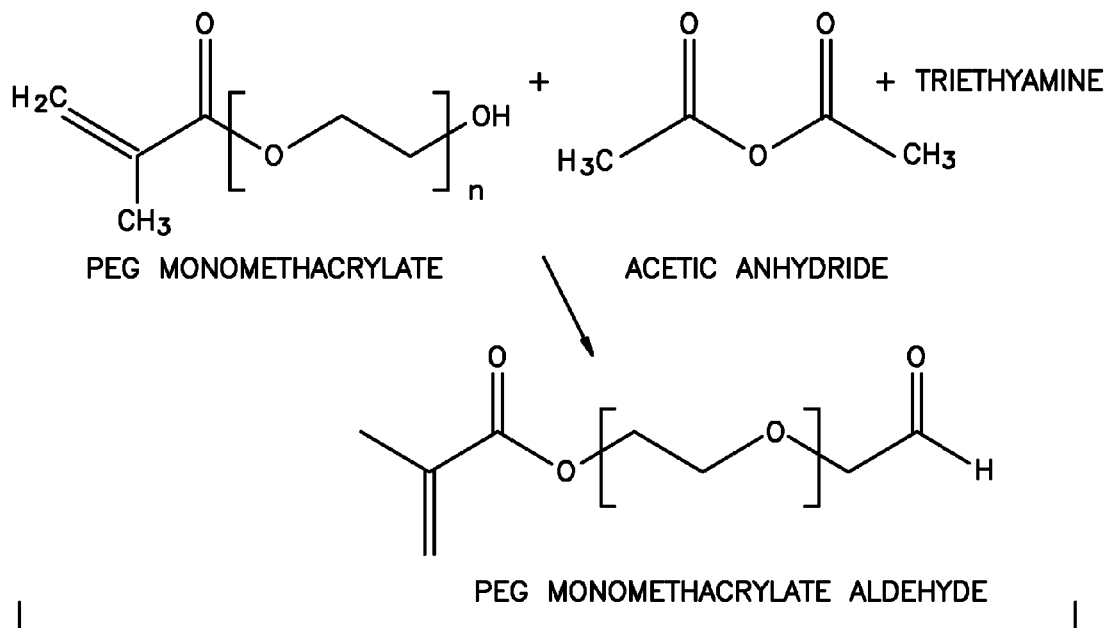
FIG. 18 is a reaction scheme for synthesis of PEG monomethacrylate aldehyde.

PEG monomethacrylate (400 g/mol) (Polysciences) was reacted in the presence of 10× molar excess acetic anhydride (Sigma-Aldrich) and triethylamine (Sigma-Aldrich) in dimethyl sulfoxide at room temperature for 48 hours (see FIG. 18). The reaction mixture was then added drop wise to ethyl ether and precipitated two more times from methylene chloride in ethyl ether.

Example V

Synthesis of PNIPAAM-PEG (4600 G/mol) with Pendant Aldehyde Groups

The PEG monomethacrylate aldehyde and NIPAAm monomer (Acros Organics) were copolymerized in methanol at 65° C. for 48 hours. The reaction was initiated by AIBN. The methanol was evaporated from the reaction mixtures after polymerization was complete. The unreacted NIPAAm monomer was removed by heating the product to 45° C. in n-hexane. The purified polymer was isolated by vacuum filtration and dried under vacuum overnight.

Example VI

In Situ Curing Example

Figure 19:
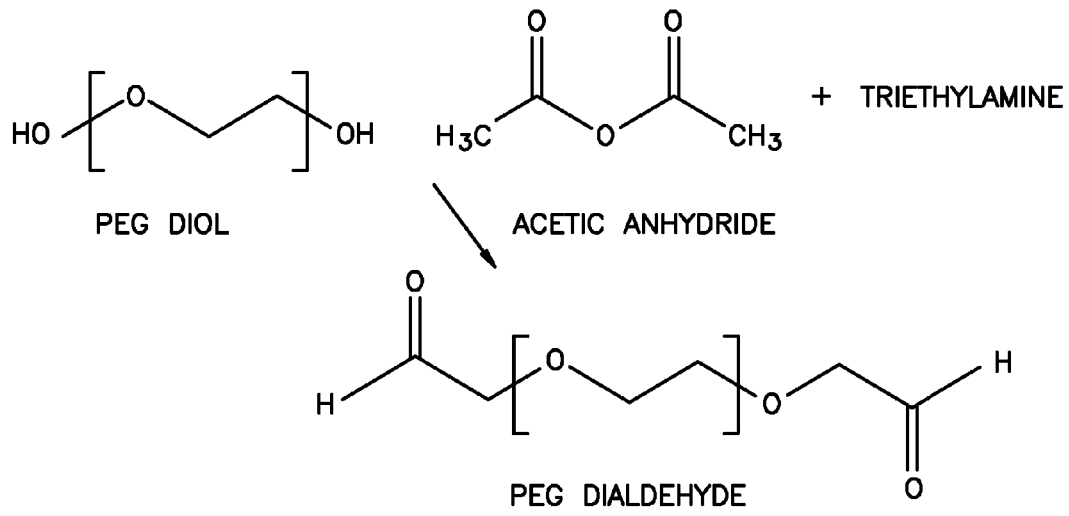
FIG. 19 is a reaction scheme for synthesis of PEG dialdehyde.

FIG. 19 shows the reaction scheme of for synthesis of PEG-dialdehyde. The reaction starts with PEG diol, acetic anhydride (Sigma-Aldrich) and triethylamine (Sigma-Aldrich) in dimethyl sulfoxide (DMSO) for 48 hours at room temperature. The reaction mixture was then added drop wise to ethyl ether and precipitated two more times from methylene chloride in ethyl ether. The reaction produces a PEG-dialdehyde with aldehyde groups on each end of the chain that can be precipitated in ether and ethyl acetate. These PEG-dialdehyde chains can be blended with PNIPAAm and/or copolymers of PNIPAAm. Crosslinking can then be initiated to form an interpenetrating network by the injection of PEI.

Figure 20:
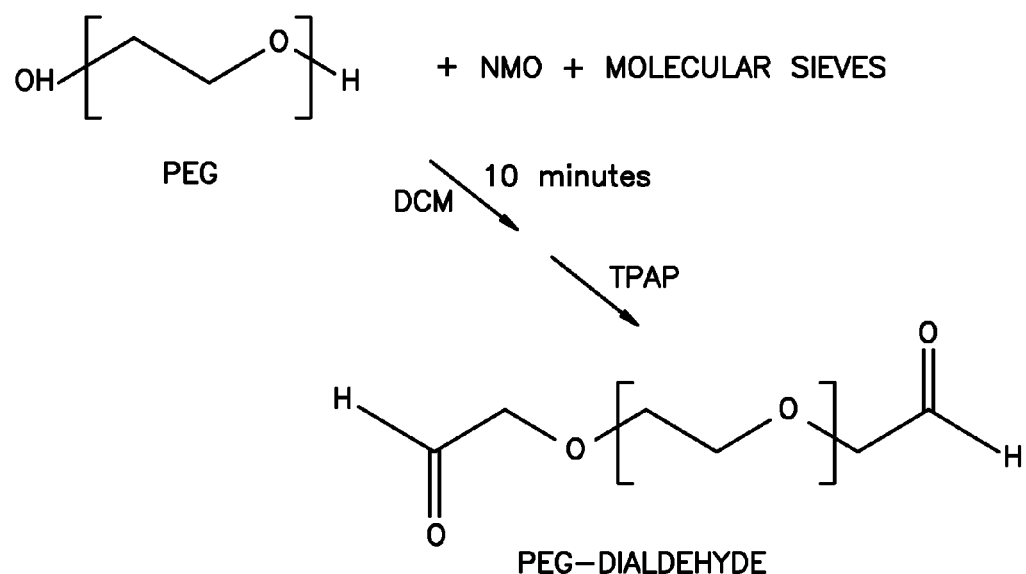
FIG. 20 is a reaction scheme for synthesis of PEG dialdehyde.

FIG. 20 shows a second method for synthesis of PEG-dialdehyde by oxidation of PEG diol.

Figure 21:
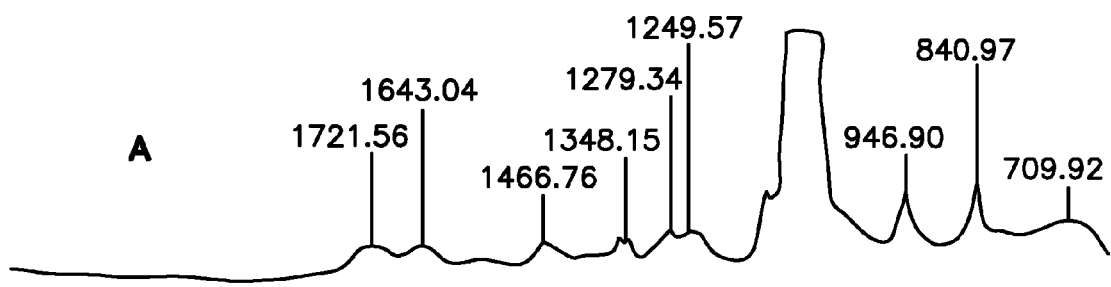
FIG. 21 is a FTIR spectrum for PEG dialdehyde.

The IR spectrum of the PEG dialdehyde shows a peak for the HC=O stretch for the aldehyde group at 1721 $cm^{-1}$ (see FIG. 21). The NMR spectrum did not have a peak at 9.5 ppm for the aldehyde proton (data not shown).

As will be appreciated by those skilled in the art, any or all of the components described herein such as, for example, the thermoresponsive polymer component, the amine-containing polymer component, the crosslinking component, etc. may be provided in sets or kits so that the surgeon may select various combinations of components to perform a repair and/or augmentation which is configured specifically for the particular needs/anatomy of a patient. It should be noted that one or more of each component may be provided in a kit or set. In some kits or sets, the same components may be provided in different amounts, compositions, etc.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

It will thus be seen that the objects set forth above, among those made apparent from the preceding description, are efficiently attained and, since certain changes may be made in carrying out the above method in the constructions set forth without departing from the spirit and scope of the invention, it is intended that all matter contained in the above description and shown in the accompanying drawings shall be interpreted as illustrative and not in the limiting sense. It is also to be understood that the following claims are intended to cover all of the generic and specific features of the invention herein described and all statements of the scope of the invention, which, as a matter of language, might be said to fall there between.

Particularly it is to be understood that in said claims, ingredients or compounds recited in the singular are intended to include compatible mixtures of such ingredients wherever the sense permits.

What is claimed is:

1. A bioadhesive thermogelling hydrogel composition for repairing or augmenting an intervertebral disc and comprising: a thermoresponsive polymer component which is poly(n-isopropyl acrylamide); an amine-containing polymer component which is poly(ethylene imine) that is further reacted with a carbonate group by the creation of stable urethane linkages; and a crosslinker which is a dialdehyde component that is selected from the group consisting of butanedial, glutaraldehyde, and mixtures thereof, and wherein the dialdehyde component is separated from the poly(ethylene imine) until the poly(n-isopropyl acrylamide, the dialdehyde component, and the poly(ethylene imine) are injected into an intervertebral disc such that the dialdehyde component crosslinks with the poly(ethylene imine) and the composition solidifies in situ, and wherein the solidified in situ composition is capable of crosslinking to tissue surrounding the composition.

2. The composition of claim 1, wherein the poly(n-isopropyl acrylamide) is copolymerized with poly(ethylene glycol) prior to be combined with the poly(ethylene imine) and glutaraldehyde.

3. The composition of claim 2, wherein the composition has an adhesion strength between about 0.20 MPa to about 0.34 MPa.

4. The composition of claim 2, wherein the poly(ethylene glycol) copolymerized poly(n-isopropyl acrylamide) comprises about 15% by weight of the composition.

5. The composition of claim 4, wherein the poly(ethylene imine) comprises about 8.5% by weight of the composition.

6. The composition of claim 1, wherein the poly (n-isopropyl acrylamide) and the poly (ethylene imine) are injected first before injection of the dialdehyde component.

7. The composition of claim 1, wherein the poly(n-isopropyl acrylamide) and the poly(ethylene imine) are simultaneously injected into the intervertebral disc.

8. A bioadhesive thermogelling hydrogel composition for an intervertebral disc and comprising: a thermoresponsive polymer component which comprises poly(n-isopropyl acrylamide) (PNIPPAm); an amine-containing polymer component which comprises poly(ethylene) imine that is further reacted with a carbonate group by the creation of stable urethane linkages; and a crosslinker which comprises a di-functional dialdehyde component that is selected from the group consisting of butanedial, glutaraldehyde, and mixtures thereof, wherein the components are injectable into an intervertebral disc where the composition solidifies in situ, wherein the aldehyde component is separated from the poly (ethylene imine) until they are injected into the intervertebral disc such that the dialdehyde component crosslinks with the poly(ethylene imine) and wherein the solidified in situ composition is capable of crosslinking to tissue surrounding the composition.

9. The composition of claim 8, wherein the thermoresponsive polymer component and the amine-containing polymer component are blended in an aqueous solution.

10. The composition of claim 8, wherein the thermoresponsive component and the amine-containing component exist as copolymers.

11. The composition of claim 8, wherein the thermoresponsive polymer component is reacted to include aldehyde groups.

12. The composition of claim 8, wherein the thermoresponsive polymer component and the amine-containing component are inserted into the intervertebral disc collectively and wherein the crosslinker is inserted into the intervertebral disc after the thermoresponsive polymer component and the amine-containing component have been inserted into the intervertebral disc.

13. The composition of claim 8, wherein the thermoresponsive polymer component and the crosslinker are inserted into the intervertebral disc collectively and wherein the amine-containing component is inserted into the intervertebral disc after the thermoresponsive polymer component and the crosslinker have been inserted into the intervertebral disc.

14. The composition of claim 8, wherein the thermoresponsive polymer component comprises homopolymers of poly-(n-ispropylacrylamide) (PNIPAAm), copolymers of poly-(n-isopropylacrylamide) (PNIPAAm) with polyethylene glycol (PEG), and mixtures thereof.

15. The composition of claim 14, wherein the thermoresponsive polymer component comprises copolymers of PNIPAAm-PEG.

16. The composition of claim 8, wherein the crosslinker is glutaraldehyde.

17. The composition of claim 8 wherein the thermoresponsive polymer component is grafted with a whole or parts of the amine-containing polymer.

\* \* \* \* \*